(12) United States Patent
Holland

(10) Patent No.: US 9,075,008 B2
(45) Date of Patent: Jul. 7, 2015

(54) PLANT TREATMENT BASED ON A WATER INVARIANT CHLOROPHYLL INDEX

(76) Inventor: Kyle H. Holland, Lincoln, NE (US)

( * ) Notice: Subject to any disclaimer, the term of this patent is extended or adjusted under 35 U.S.C. 154(b) by 849 days.

(21) Appl. No.: 12/896,460

(22) Filed: Oct. 1, 2010

(65) Prior Publication Data

US 2011/0047867 A1 Mar. 3, 2011

Related U.S. Application Data

(63) Continuation-in-part of application No. 12/108,371, filed on Apr. 23, 2008, which is a continuation-in-part of application No. 10/703,256, filed on Nov. 7, 2003, now Pat. No. 7,408,145.

(60) Provisional application No. 60/925,831, filed on Apr. 23, 2007.

(51) Int. Cl.
*G01V 8/20* (2006.01)
*G01J 3/51* (2006.01)
*G01N 21/55* (2014.01)
*G01J 3/10* (2006.01)
*G01J 3/36* (2006.01)

(Continued)

(52) U.S. Cl.
CPC . *G01N 21/55* (2013.01); *G01J 3/10* (2013.01); *G01J 3/36* (2013.01); *G01N 21/31* (2013.01); *G01N 21/3563* (2013.01); *G01N 2021/3155* (2013.01); *G01N 2021/635* (2013.01); *G01N 2021/8466* (2013.01); *G01N 2201/1244* (2013.01)

(58) Field of Classification Search
CPC ..... A01M 7/00; A01M 7/005; A01M 7/0098; A01M 21/04; A01M 21/043; A01M 21/046; A01G 7/00; A01G 7/04; A01G 7/02; A01G 7/045; A01G 7/06; A01G 25/00; A01G 25/02; A01G 25/023; B05B 1/00; B05B 1/005; B05B 1/02; B05B 1/12; B05B 1/14
USPC ............ 250/221, 214 AL, 208.1, 226; 47/1.7, 47/58.1 R, 58.1 LS; 356/317, 318, 417, 356/447, 445; 382/110
See application file for complete search history.

(56) References Cited

U.S. PATENT DOCUMENTS 3,443,072 A 5/1969 Gibbs
3,910,701 A 10/1975 Hendersen et al.
(Continued)

OTHER PUBLICATIONS

Wu et al., Estimating Chlorophyll Content from Hyperspectral Vegetation Indices: Modeling and Validation, Jul. 2008, pp. 1230-1241.*
(Continued)

*Primary Examiner* — Pascal M Bui Pho
(74) *Attorney, Agent, or Firm* — McKee, Voorhees & Sease, PLC

(57) ABSTRACT

A method and system of treating plants is provided. The method includes measuring optical properties of a plant using a plurality of spectral bands. The method further includes calculating in a computational device at least two vegetative indexes using the optical properties, each of the at least two vegetative indexes correlating to one or more plant growth parameters. The method further includes calculating in the computational device a water invariant chlorophyll index from at least two vegetative indexes using the plurality of spectral bands. The also provides for treating one or more of the plants based on the water invariant chlorophyll index.

18 Claims, 9 Drawing Sheets

(51) Int. Cl.
  *G01N 21/31*    (2006.01)
  *G01N 21/3563*  (2014.01)
  *G01N 21/63*    (2006.01)
  *G01N 21/84*    (2006.01)

(56) References Cited

U.S. PATENT DOCUMENTS

| | | | |
|---|---|---|---|
| 4,055,768 A | 10/1977 | Bromberg | |
| 4,369,886 A | 1/1983 | Lane et al. | |
| 4,518,253 A | 5/1985 | Takahashi | |
| 4,628,454 A | 12/1986 | Ito | |
| 4,926,170 A | 5/1990 | Beggs et al. | |
| 4,986,665 A | 1/1991 | Yamanishi et al. | |
| 5,025,150 A | 6/1991 | Oldham et al. | |
| 5,144,767 A | 9/1992 | McCloy et al. | |
| 5,281,798 A | 1/1994 | Hamm et al. | |
| 5,296,702 A | 3/1994 | Beck et al. | |
| 5,389,781 A * | 2/1995 | Beck et al. | 250/226 |
| 5,585,626 A | 12/1996 | Beck et al. | |
| 5,763,873 A | 6/1998 | Beck et al. | |
| 5,789,741 A | 8/1998 | Kinter et al. | |
| 5,809,440 A | 9/1998 | Beck et al. | |
| 5,833,144 A | 11/1998 | Kinter | |
| 5,837,997 A | 11/1998 | Beck | |
| 6,160,902 A * | 12/2000 | Dickson et al. | 382/110 |
| 6,393,927 B1 | 5/2002 | Biggs | |
| 6,596,996 B1 | 7/2003 | Stone et al. | |
| 7,049,597 B2 | 5/2006 | Bodkin | |
| 7,058,197 B1 | 6/2006 | McGuire et al. | |
| 7,746,452 B2 * | 6/2010 | Fuchigami et al. | 356/73 |
| 8,135,178 B2 | 3/2012 | Hendrickson et al. | |
| 2004/0119020 A1 | 6/2004 | Bodkin | |

OTHER PUBLICATIONS

Mascarini et al., Leaf Area Index, Water Index, and Red: Far Red Ratio Calculated by Spectral Reflectance and its Relation to Plant Architecture and Cut Rose Production, May 2006, pp. 313-319.*

Marvin L. Stone and Mark Zachos, Application of J1939 Networks in Agricultural Equipment, Oklahoma State University Dearborn Group, Stillwater, Oklahoma Farmington Hills, Michigan, http://biosystems.okstate.edu/home/mstone/ag.J1939.htm.

Aronson, Milton H., "Low-Level Measurements-8 Lock-in and Carrier Amplifiers", Measurements and Data Corporation, pp. C1-C15.

Gage, S. Evans et al., Optoelectronics Applications Manual, 1977. McGraw-Hill Book Co.

Haggar, R.J. et al., "A Prototype Hand-Held Patch Sprayer for Killing Weeds, Activated by Spectral Difference in Crop/Weed Canopies", Agricultural Research Counsel, Nov. 15, 1982, pp. 349-358.

Haggar, R.J. et al., "Measuring Spectral Differences in Vegetation Canopies by a Reflectance Ratio Meter", Weed Research, 1984 vol. 24, pp. 59-65.

Hooper, A. W. et al., "A Photoelectric Sensor for Distinguishing between Plant Material and Soil" J. Agric. Engng. Res. (1976) 21, pp. 145-155.

Knipling, E.B., "Physical and Physiological Basis for the Visible and Near-Infrared Radiation from Vegetation", American Elsevier Publishing Company, Inc. 1970, pp. 155-159.

Palmer, J. et al., "Automatic Control of Sugar Beet Singling and Thinning by Means of an On-line Digital Computer", J. Agric. Eng. Res., (1971), vol. 16 (2), pp. 107-125.

Ritchie, J.C. et al., "Airborne laser measurements of rangeland canopy cover and distribution", J. Range Manage, Mar. 1992, 45:189-193.

Searcy, S. W. et al., "Measurement of Agricultural Field Location Using Microwave Frequency Triangulation" Computers and Electronics in Agriculture (1990), vol. 4, pp. 209-233.

Stafford, J. V. et al., "A Portable Infra-red Moisture Meter for Agricultural and Food Materials: Part 1, Instrument Development", J. Agric. Eng. Res. (1989), 43:45-46.

Thompson, J.F. et al., "Potential for Automatic Weed Detection and Selective Herbicide Application", Crop Protection (1991), vol. 10, p. 254-259.

Zygielbaum, Arthur I. et al., "Non-destructive detection of water stress and estimation of relative water content in maize", Geophysical Research Letters, vol. 36, L12403, pp. 1-4, 2009.

Girma, Kefyalew et al., "Nitrogen Accumulation in Shoots as a Function of Growth Stage of Corn and Winter Wheat", Journal of Plant Nutrition, Dec. 1, 2010, 34:2, 165-182.

Hodgen, P. J. et al., "Relationship Between Response Indices Measured In-Season and at Harvest in Winter Wheat", Journal of Plant Nutrition, 2005, 28: 221-235.

Holland, K. H. et al., "Derivation of a Variable Rate Nitrogen Application Model for In-Season Fertilization of Corn", Agronomy Journal, 2010, vol. 102, Issue 5, pp. 1415-1424.

Raun, William R. et al., "Independence of yield potential and crop nitrogen response" Precision Agri., Oct. 2, 2010, DOI 10.1007/s11119-010-9196-z; Springer Science+Business Media, LLC, 2010.

Raun, William R. et al., "Chapter 10—Temporally and Spatially Dependent Nitrogen Management for Diverse Environments" c10.indd, Jan. 22, 2009, pp. 203-214.

Shanahan, J.F. et al., "Responsive in-season nitrogen management for cereals", Computers and Electronics in Agriculture 61 (2008) pp. 51-62.

* cited by examiner

PLANT TREATMENT BASED ON A WATER INVARIANT CHLOROPHYLL INDEX

CROSS-REFERENCE TO RELATED APPLICATIONS

This application is a continuation-in-part of U.S. patent application Ser. No. 12/108,371 filed Apr. 23, 2008, which is a continuation-in-part of U.S. patent application Ser. No. 10/703,256 filed Nov. 7, 2003, which is now U.S. Pat. No. 7,408,145 issued on Aug. 5, 2008 and which also claims priority to United States Provisional Application No. 60/925,831 filed Apr. 23, 2007, all of which are herein incorporated by reference in their entireties.

FIELD OF THE INVENTION

This invention relates to a structure and a method for determining changes in the chlorophyll status of a plant via remote sensing of the plant's reflectance spectrum spanning from approximately 400 nm to 1200 nm.

BACKGROUND OF THE INVENTION

Techniques to remotely measure crop status have historically include the use of a spectroradiometer and other instruments (Bausch et al. 1994; Chappelle et al. 1992; Maas and Dunlap, 1989), aerial photography (Benton et al, 1976), and satellite imagery.

The techniques listed above are not without their limitations. For example, early research by Resource21 ™ determined that during the optimal fly over times between 10 a.m. and 11 a.m. for satellite imaging, cloud cover had adverse affects on visibility. It was found that during the 10 a.m. to 11 a.m. time frame, fields in Colorado were visible approximately 80% of the time while eastern Nebraska fields were visible approximately 50% of the time. This trend in decreased visibility continued the farther east that data was collected. Also, spatial resolution for satellite imagery is poor (Landsat, 20 meter and panchromatic, 10 meter). Similar problems plague aerial photographic methods as well. While aerial imagery has better spatial resolution (typically less than 3 meters) than satellite imaging, partial cloud cover can shade sections of fields giving biased or incorrect reflectance measurements. Both techniques, however, suffer from the need for extensive data processing (performed by third party providers at high cost and long lead time) and geo-referencing issues. Even with spectroradiometric methods using sunlight as the ambient light source, cloud cover and time of day (8 a.m. to 8 p.m.) demands limit the mainstream acceptance of the technology for addressing the nitrogen rate over-loading problem.

Vehicle-mounted, active sensing technologies overcome the limitations of the passive technologies listed above by utilizing artificially generated light to irradiate a plant canopy and measure a portion of this light that is reflected off the canopy, much like the passive sensing instrumentation. Active sensors can have either steady-state or modulated light sources. With steady-state light illumination, care must be taken to adequately shield the measurement scene (typically a leaf) from ambient light such as in the case of spectrophotometric measurements utilizing a halogen lamp. However, sensors with modulated light sources can be operated without concern for ambient background illumination. With a modulated active sensor, the modulated radiation is reflected from the target and measured by the sensor's detection hardware. Electrical circuits within the sensor are able to differentiate between the modulated portion of the reflectance and ambient background light. This unique feature of active sensors is why they can operate equally well under all lighting conditions. Active sensors are sometimes referred to as real-time or on-the-go sensors. This simply means that the data or measurements produced by the sensors can be utilized immediately for performing agricultural operations such as applying herbicide or fertilizer.

Active plant canopy sensors have a long history dating back almost 70 years. One of the earliest active electro-optical sensors was developed by Ferté and Balp (U.S. Pat. No. 2,177,803). This sensor was designed to be spectrally sensitive to a plant's carotenoid peak located at 550 nm for the intended purpose of detecting plants and selective thinning. The detection system utilized two phototubes each fitted with spectrally selective filters. One filter was colored with methyl green pigment to give the associated detector a spectral sensitivity to vegetation with a spectral peak located at 535 nm while the other filter was colored with rhodamine B to create a notch filter to block green light. The interplay between the optical signals sensed by the detection circuitry was utilized by the system to activate a plant thinning device.

Another early active sensor was developed by Marihart (U.S. Pat. No. 2,682,132). This particular sensor was vehicle mounted and was developed for the selective application of herbicides and fertilizer. The sensing system utilized a modulated light source consisting of a fluorescent lamp and a phototube connected to an inductor-capacitor tuned amplifier to measure light reflected from the plant canopy. Spectral selectivity was performed via the use of color filters in front of either the detector or the light source.

In 1969, Palmer et al. developed a sugar beet singling and thinning system to automatically thin plant populations. This instrument incorporated four optically modulated sensors connected to a PDP-8 minicomputer mounted to a tractor/mower. Plant distribution was detected via two photomultiplier tubes fitted with optical band pass filters inside each sensor. The center wavelengths for the filters were 630 nm and 810 nm with each filter having an apparent bandwidth of roughly 60 nm. The minicomputer was programmed to create a 2-dimensional "kill map" of plants to be eliminated. When a plant to be eliminated was detected, the system would respond by spraying the plant with a non-selective herbicide.

During the time period spanning from 1975 to 2002, fully solid-state plant status and weed sensors were developed. These sensors utilized LED's to actively illuminate plant canopies in order to overcome the limitations of lamp-based and passive illumination methods. Henderson and Grafton (U.S. Pat. No. 3,902,701) developed one of the first active sensor instruments to use LED's as an illumination source. The instrument was designed to be mobile with an intended use to measure leaf reflectance characteristics and relate this reflectance to plant health and status. Stafford et al. (1989) developed a portable handheld sensor to measure turf moisture content. This instrument contained two near infrared (NIR) monochromatic LED's with one LED source emitting 940 nm light and the other 1150 nm light. Subsequently, Beck and Vyse (U.S. Pat. No. 5,292,702) developed an active weed sensor, much like the Henderson sensor, incorporating two LED light sources with one LED source emitting 670 nm light and the other 750 nm light (WeedSeeker by Patchen, Ukiah, Calif.). Stone et al. (U.S. Pat. No. 6,596,996) developed a dual wavelength active light sensor, essentially a form of the Henderson and Beck patents, for the purpose of quantitative biomass determination while Holland (U.S. Pat. No. 7,408,145) developed a plant biomass sensor utilizing a novel polychromatic LED light source. For all the aforementioned solid state sensors, the light sources were modulated and detected reflectance signals were demodulated synchronously. Reusch in European Patent EP 1 429 594 and his paper submitted to the 6$^{th}$ European Conference on Precision Agriculture discloses a technique to use halogen and flash lamp techniques for active illumination. The instrumentation taught in these documents are similar to the instrument disclosed by Palmer and Owens (1969). It should be noted concerning spectral selectivity, that Holland (U.S. Pat. No. 7,408,145) describes a device that addresses the concerns Reusch has argued regarding LED technology.

SUMMARY OF THE INVENTION

The new sensor of the present invention overcomes the time-of-day and fair weather limitations of passive technologies by incorporating its own radiant source and by rejecting the influence of ambient light on the measured canopy reflectance. Unlike passive sensor technology, this sensor will be able to operate under completely dark or full sun conditions.

Additionally, the new sensor apparatus is an improvement both in performance and cost over competing active-sensor technologies commercially available. Furthermore it improves on prior art by allowing sensors to be developed that have wavelength selectivity, improved light source performance and life, and detection means and signal processing.

As discussed above, the invention presented here will be advantageous in a number of commercial applications. For site-specific agricultural applications, the developed sensor would allow the producer to reduce the amount of nitrogen fertilizer applied to a crop or facilitate spoon-feeding the crop during the growing season, thus having the potential for lowering production costs and enhancing environmental quality. Also, by being able to determine the appropriate fertilizer needs of the crop at any given location in the field, the producer can apply only the fertilizer needed to prevent yield loss or degradation of product quality (i.e., protein content in wheat and barley or sugar content in sugar beets). Subsequently, decreased fertilizer rates will substantially lower nitrogen runoff and leaching losses, which will improve the health of our watersheds, waterways, lakes, and oceans. In addition, data produced by the sensor may be used to produce relative yield maps for forecasting crop production. As for turf grass applications, the sensor technology would allow turf managers to map changes occurring on turf landscapes or for monitoring the status of turf quality.

When incorporated into variable rate applicator and/or sprayers systems, the present invention significantly reduces the use of fertilizers by precisely applying agricultural products to individual plants to be treated or eliminated. Moreover, the present invention is operable under a wide variety of conditions including cloudy conditions, bright sunlight, artificial illumination, or even total darkness. The advantage to the producer is that field operations do not have to be timed to daytime sunlight hours for operation.

All embodiments of the invention can be used in two primary ways. The first method of use includes the application of the invention to handheld instrumentation. Here the invention is utilized to measure plant canopies held in hand by a producer, turf manager, researcher, and the like. The invention may include the use of GPS for geo-referencing data collected by the invention. A second method of use includes applications where the sensor is mounted on a moving object such as a tractor, mower, center pivot/linear irrigator, or the like. Again, data may be geo-referenced using GPS for mapping and data layer (GPS maps, soil maps, etc.) integration. Problem areas can be logged and reviewed later by the producer or land manager for analysis and site management decisions.

An object of the invention is to provide a sensor for remotely sensing plant status using biophysical and biochemical properties of the plant thereby allowing selective monitoring, elimination, or treatment of individual plants.

This and other objects of the invention will be made apparent to those skilled in the art upon a review of this specification, the associated drawings and the appended claims.

According to one aspect of the present invention, a method of treating plants is provided. The method includes measuring optical properties of a plant using a plurality of spectral bands. The method further includes calculating in a computational device at least two vegetative indexes using the optical properties, each of the at least two vegetative indexes correlating to one or more plant growth parameters. The method further includes calculating in the computational device a water invariant chlorophyll index from at least two vegetative indexes using the plurality of spectral bands. The also provides for treating one or more of the plants based on the water invariant chlorophyll index.

According to another aspect of the present invention, a method of treating plants includes measuring optical properties of one or more plants across a plurality of spectral bands, and calculating in a computational device at least two vegetative indexes using the optical properties, each of the at least two vegetative indexes correlating to one or more plant growth parameters. The method further includes calculating in the computational device a water invariant chlorophyll index from at least two vegetative indexes using the plurality of spectral bands. The method also includes treating the plants based on the water invariant chlorophyll index.

According to another aspect of the present invention, a system for treating plants includes an optical sensing system configured to measure optical properties of one or more plants across a plurality of spectral bands. The system also includes an applicator for selectively applying treatment to the plants. The system also includes an intelligent control or controller which is operatively connected to the optical sensing system and the applicator and configured to (a) calculate at least two vegetative indexes using the optical properties, each of the at least two vegetative indexes correlating to one or more plant growth parameters, (b) calculate a water invariant chlorophyll index from at least two vegetative indexes using the plurality of spectral bands, and (c) control the applicator to provide for selectively applying treatment to the plants based on the water invariant chlorophyll index.

According to another aspect of the present invention, a method for measuring a plant's reflectance is provided. The method includes modulating a light source comprised of one or more LEDS that emit light in the spectral range of 350 nm to 480 nm having a phosphorescent coating, and detecting light originating from the light source reflected off of the plant in the presence of ambient light in one or more spectrally sensitive photodetectors.

According to another aspect of the present invention, a method of treating plants includes measuring optical properties of a plant using at least three spectral bands, determining by a computational device a treatment for one or more of the plants using the optical properties, and
applying the treatment to the one or more of the plants.

According to another aspect of the present invention, a system for treating plants includes an optical sensing system configured to measure optical properties of one or more plants across a plurality of spectral bands, an applicator for selectively applying treatment to the plants, and a controller operatively connected to the optical sensing system and the applicator and configured to control the application of the treatment based on properties of the one or more plants determined from the optical properties, and one or more indexes that relate the properties of the one or more plants to the optical properties.

According to another aspect of the present invention, a method of treating plants includes measuring optical properties of a plant using a plurality of spectral bands, and calculating in a computational device at least two vegetative indexes using the optical properties, each of the at least two vegetative indexes correlating to one or more plant growth parameters, wherein a first of the vegetative indexes is used for low leaf area index and a second of the vegetative indexes is used for a high leaf area index.

DETAILED DESCRIPTION

The following contains a description for a sensor that remotely measures plant canopy chlorophyll content independent of soil reflectance and ambient illumination levels. The sensor can be used in stand-alone instrumentation configurations or in a network of sensors mounted to a vehicle or moving apparatus for on-the-go remote sensing applications. The following description of the invention is meant to be illustrative and not limiting. Other embodiments will be obvious in view of this invention.

Figure 1:
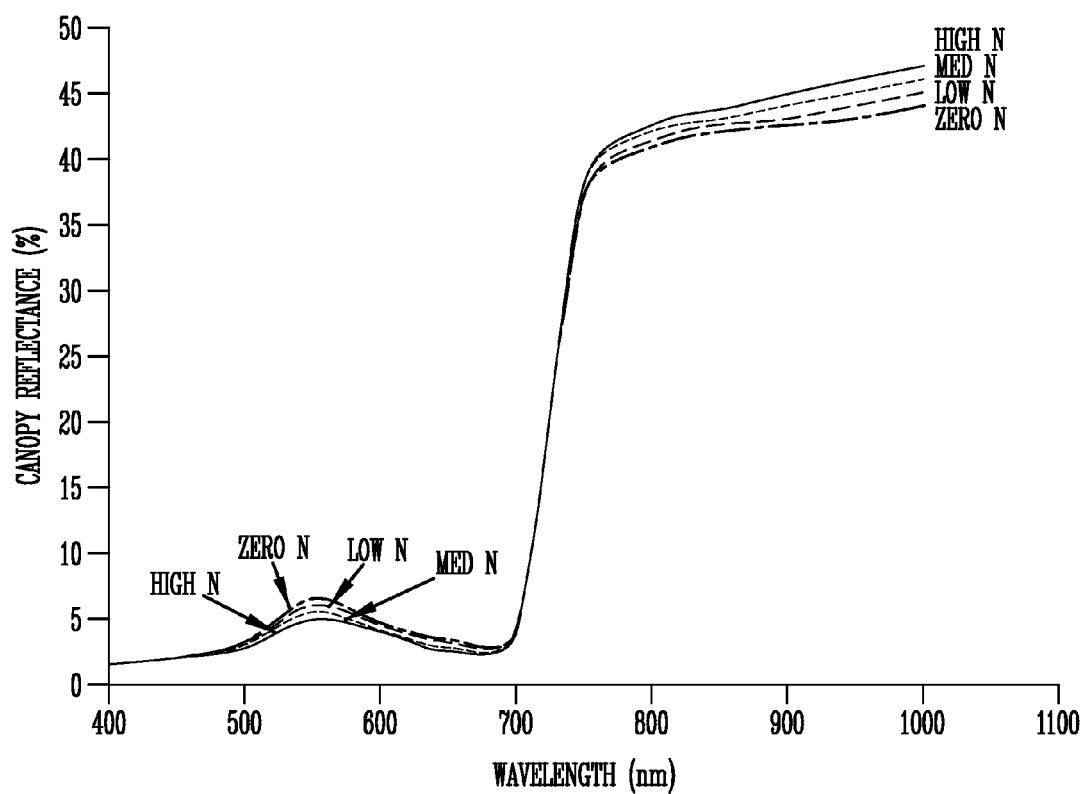
FIG. 1 illustrates plant reflectance curves over the visible and near infrared portion of the spectrum with the red-edge portion of the spectrum emphasized.

The positive relationship between leaf greenness and crop nitrogen (N) status means it should be possible to determine crop N requirements based on reflectance data collected from the crop canopy (Walberg et al., 1982; Girardin et al., 1985; Hinzman et al., 1986; Dwyer et al., 1991) and leaves (McMurtrey et al., 1994), see FIG. 1. Plants with increased levels of N typically have more chlorophyll (Inada, 1965; Rodolfo and Peregrina, 1962; Al-Abbas et al., 1974; Wolfe et al., 1988) and greater rates of photosynthesis (Sinclair and Horie, 1989). Hence, plants that appear a darker green are perceived to be healthier than N deficient plants and as such healthier plants reflectance less light in the visible portion of the spectrum (400 to 700 nm) and reflect more light in the near infrared (>700 nm), see FIG. 2.

Figure 2:
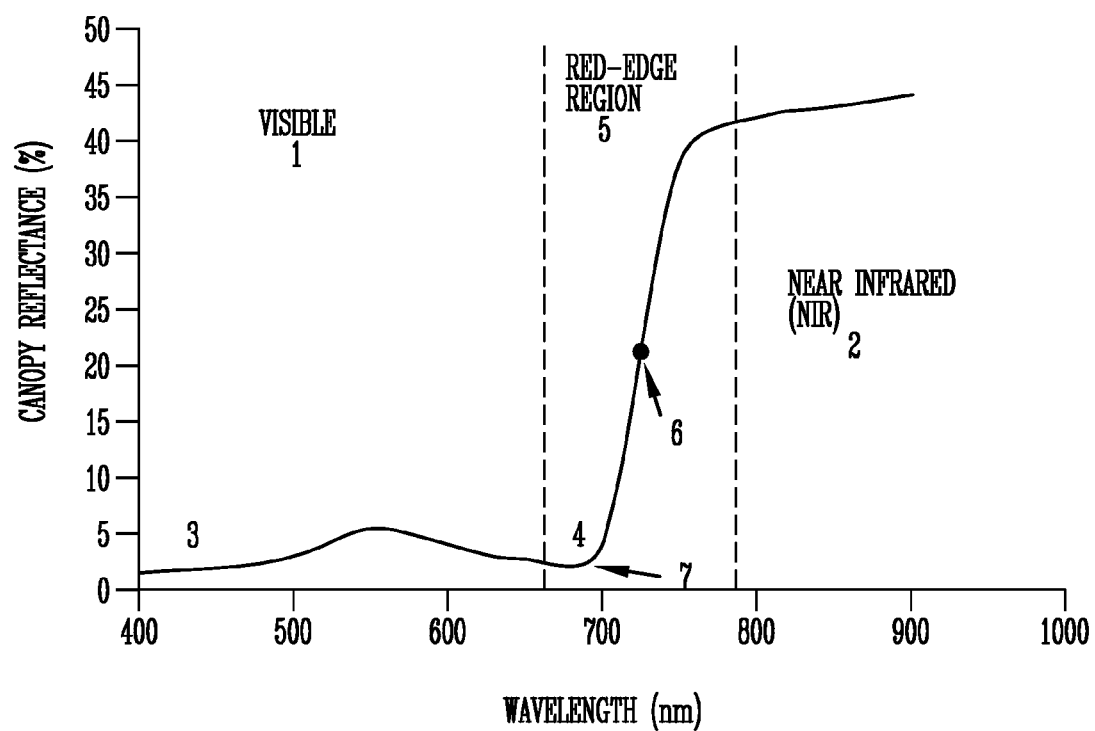
FIG. 2 illustrates the effect of nitrogen rate on the plant reflectance curve over the visible and near infrared portion of the spectrum.

Chlorophyll in leaves absorbs strongly in the blue 3 and red 4 regions of the spectrum (460 nm and 670 nm) and as the wavelengths increase past 670 nm the leaves begin to strongly reflect infrared light, see FIG. 2. The transition region between the photosynthetic portion 1 (400 nm to 670 nm) and the biomass portion 2 (>780 nm) of a plant's reflectance spectrum is sometimes referred to as the red-edge region 5. It has been reported in literature that the wavelength where the maxima of the derivative 6 for the red-edge band occurs is strongly correlated to changes in the chlorophyll status of a plant. Guyot and Baret (1988) developed an algebraic relationship expressing the wavelength of the red-edge inflection point (REIP) 6, sometimes referred to as the red edge position (REP), using four reflectance bands spanning from 670 nm to 780 nm. The usefulness of measuring red-edge reflectance spectra, and subsequently determining the inflection point's wavelength position, is that the chlorophyll status of the plant can be measured independently of soil background interference. That is, the chlorophyll status as denoted by shifts in the red-edge inflection point, is independent of the slope of the vegetative reflectance curve and has reduced sensitivity to soil and biomass reflectance characteristics. Shifts in the value of the inflection point are directly related to the chlorophyll status (and water content) of the plant with chlorophyll content being closely related to nutrient status. Another useful red edge parameter is the red well position 7 (RWP). This is the point on the vegetation reflectance curve that represents the plants minimum reflectance, i.e., the wavelength of maximum chlorophyll absorption. This parameter, like the REIP, is also useful in determining changes in a plant's chlorophyll status. Other vegetative indices are also available for plant N status determination that solely rely on visible wavebands (400 nm to 700 nm). For example the Visible Atmospherically Resistant Index (V ARI) utilizes reflectances at 550 nm (green light) and 670 nm (red light). Indices of this form can provide significant information pertaining to crop phenology.

The general embodiment of the invention can be utilized to measure plant vegetation reflection. In this embodiment, a low-color temperature white LED emitter(s) provide coincident beam of light; the beam of light is substantially in the vegetative reflectance spectrum (400 nm to 900 nm) and is sequenced on and off. The light source may be composed most preferably of one or more white LED emitters. The emitted LED beam illuminates a surface area on the plant's canopy, which may include bare ground and desired plants. The reflected light signals are then detected by an array of spectrally sensitive photo detectors fitted with filters. In a second embodiment, a high-color temperature white LED emitter(s) provide coincident beam of light; the beam of light is substantially in the vegetative reflectance spectrum (400 nm to 750 nm) and is sequenced on and off. The light source may be composed most preferably of one or more white LED emitters. As with the first embodiment, the LED beam illuminates a surface area on the plant's canopy, which may include bare ground and desired plants. The reflected light signals are then detected by an array of spectrally sensitive photo detectors fitted with filters. Each embodiment utilizes a controller for analyzing reflectance signals measured by the instruments and, assuming a plant is detected, responds by activating a device to take some action with respect to the plant or stores the analyzed signal with corresponding DGPS position in the controller's memory for later analysis. A number of actions may be taken by the controller. If the plant is a crop that is determined to be lacking in nutrient, the desired action may be to apply fertilizer.

Additionally, if the plant under test is a turf landscape, such as found on golf courses and sporting fields, plant chlorophyll and/or biomass may be mapped and geo-located using GPS for later, comparative analysis.

In the first embodiment listed above, the visible wave bands (540 nm to 680 nm) and the long wave near infrared bands (760 nm to 900 nm) may be utilized to calculate classic biomass vegetative indexes such as normalized difference vegetative index (NDVI), simple ratio index (SRI), etc. Additionally other unique vegetative indices, sensitive to chlorophyll can be formulated utilizing the wavebands along the red edge. For example, one could use a 730 nm LED and a 780 nm LED to illuminate the canopy in order to measure a plant's chlorophyll content. The reflectance ratio of these two wavebands is proportional to the chlorophyll status of the plant. Albeit, this ratio may be somewhat sensitive to soil background interference, it will produce good data for canopies with LAI's greater than 2, that is, canopies that have more complete closure.

Prior art cited in U.S. Pat. No. 3,910,701 teaches the use of multiple LED wavelengths for plant status determination and the use of wavelength differentials (slopes) for comparative determination of plant status. This art, however, makes no distinction on the use the red-edge portion of a plant's reflectance spectrum for qualitative chlorophyll assessment. Prior art cited in U.S. Pat. No. 5,789,741 make no distinction with respect to chlorophyll content measurement but rather refer to changes in the slope of the vegetative reflectance spectrum as being indicative of the presence or absence of plant material as compared with soil background reflectivity. The resultant measurement made by the invention of '741 will be heavily influenced by soil background interference. Furthermore, this invention does not incorporate the spectral reflectance around the red-edge portion of vegetative reflectance curve but rather detects slope changes as they deviate from the soil background line (but still heavily influenced by soil background interference); one slope calculated from 600 nm to 670 nm and the other from 670 nm to 780 nm. As such, one trained in the art will note that data produced by this method (U.S. Pat. No. 5,789,741) offers limited benefit over biomass calculation methodologies via data produced by prior art referenced in U.S. Pat. Nos. 5,296,702, 5,389,781, 5,585,626 and 6,596,996. Reusch teaches a device in European Patent that uses flash lamp and halogen technology light source technology. However, these light source technologies suffer from a number of problems. It is rather impractical to utilize incandescent or halogen lamps due to the need to mechanical modulate light emitting from light sources of this type. Flash lamp technology could be utilized, however, but their use will be limited in performance due to the low modulation and demodulation rates that are achievable with such an illumination system (typically less than 100 Hz). Both lamp technologies suffer from rather short working lifetimes as well as having potentially poor spectral stability. The problems associated with flash lamp technology include, but are not limited too, are: poor mechanical stability short lifetime typically less than 3000 to 7000 hrs, poor spectral stability; although lamps, may deliver repeatable total energy, spectral band energy may fluctuate from flash to flash, poor modulation performance typically less than 100 flashes per second, high cost; cost factors associated with high energy flash lamps will limit commercial applicability, low modulation rates will result in poor signal-to-noise performance.

The problems associated with halogen lamp technology include, but not limited too, are: poor mechanical stability, short lifetime; typically less than 1000 to 2000 hrs, poor spectral stability; partly due to envelope plating from filament evaporation, can not be easily modulated (electrical modulation limits modulation rates to less than 2 Hz). Typically one would have to modulate via mechanical means for example by chopping the light using a slotted disc. Mechanical modulation schemes are both costly and unreliable, especially in high vibration environments such as those found on farm vehicles. Also, to note, both flash and halogen lamp technologies require substantially more power to operate than competing LED technologies.

While each of the two embodiments previously discussed have different spectral bands of illumination, the fundamental electronic instrumentation required to realize the two devices share many common features and in many ways are essentially the same. A discussion of the electro-optic elements required to realize each of the embodiments follows.

Figure 3:
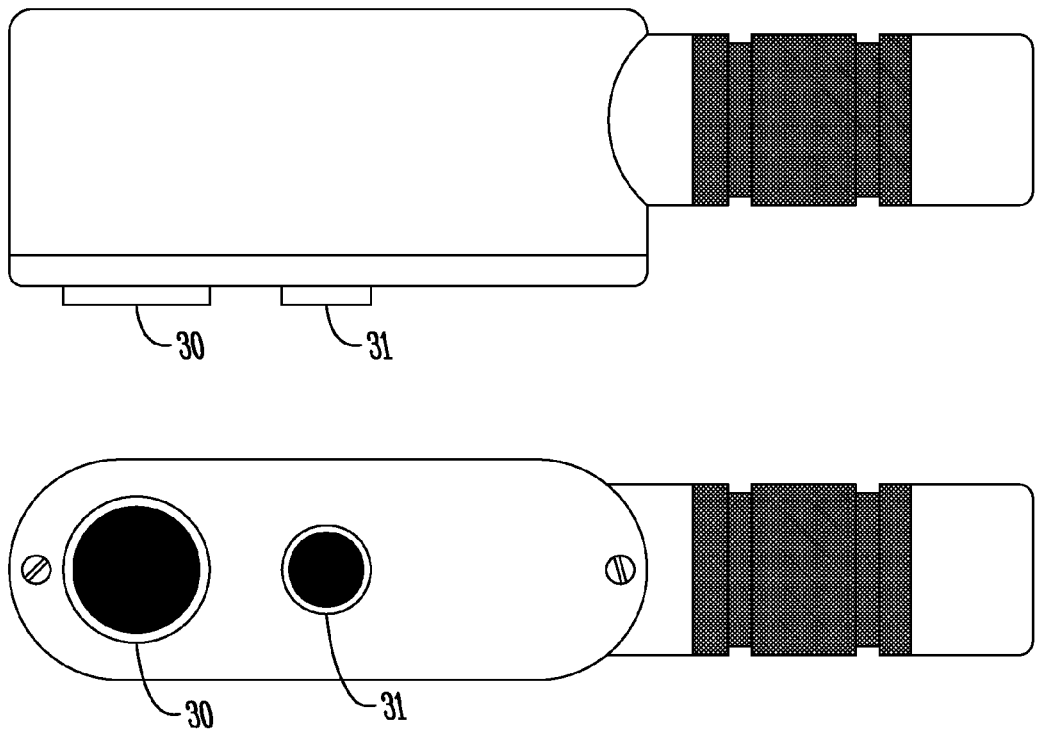
FIG. 3 shows a diagram of the inventions mechanical enclosure.

FIG. 3 shows a diagram of the sensor enclosure. The enclosure facilitates the protection of the electronic circuitry while providing optical emission and reception ports for the light source and the light detector components, respectively, of the sensor. Port 30 in FIG. 3 is the emitter port of the sensor while port 31 is the detector port of the sensor. Detector port 31 can also be a plurality of ports to facilitate multiple detector channels or the light can be split into multiple beams internally to the housing for multiple detector channels.

Port 30 and port 31 can facilitate various types of optical components to concentrate and collect optical energy. The type of optics used by the sensor can include lens, mirrors, optical flats, filters, and diffusers. The type of optics selected for the emitter and detector optics depends on the application; that is, the required field of view, the height the sensor will be operated above the plant canopy, the required cost of the sensor all may play a part in the design of the sensor's optical arrangement. The sensor can operate at a distance of ½ foot and up to 10 s of feet from the plant canopy or surface of interest but is not limited to this specific range. To those skilled in the art it should be readily apparent that fore optics on the emission side and the detection side can take on many forms.

For example, a useful optically adaptation on the detector side of the optical arrangement would be to encapsulate the detector optics (filters and detectors). The outer optical surface would have a convex surface spaced from the plane of the photodiode so as to create an afocal or nearly afocal optical arrangement. This preferred mode of construction improves the optical energy collection performance of the filter/diode combination while sealing the optical path from dust and water vapor condensation.

On the emission side of the sensor, there are a number of ways in which to shape and direct the light beam emitting from the sensor body. For instance, if one wishes to generate a line pattern from the sensors light source, preferably a bank of LEDs, one could place a cylindrical lens in front of this light source spaced appropriately so as to image a line of illumination in the field of view of the detection optics.

Alternately, a circular or ellipsoidal area of irradiance can be produced using only the encapsulation optics of an LED or an array of LEDs. In this instance, the beam pattern produced by the source is defined by the spatial irradiance distribution of each individual LED. No additional collimation or focusing optics is incorporated. Encapsulated LEDs can be purchased commercially that have spatial distribution angles of 4 degrees to almost 180 degrees. Most preferably, it is best to collimate the light emitted from an LED in order to maintain a light beam with localized irradiance over distance. In this case the LED or LED array would be spaced an appropriate distance from a convex lens (or concave mirror) to form an afocal or nearly afocal optical system. The resulting optical system will produce a light beam that will be collimated along the optical axis of the light source resulting in areas of illumination with high radiance.

Figure 4:
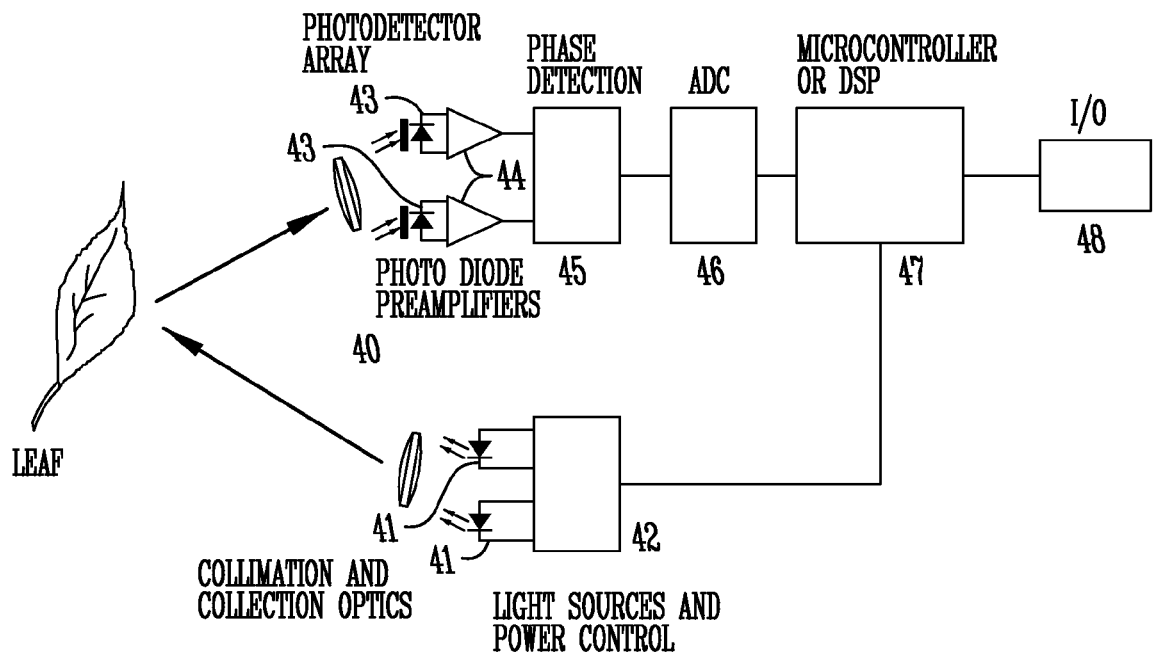
FIG. 4 shows the functional block diagram of a typical sensor embodiment.

FIG. 4 shows a system diagram typical for the many embodiments of the invention. The sensor is composed of optics to facilitate optical energy collimation and collection, a modulated light source 41 comprised of one or many banks of polychromatic LEDs and/or monochromatic LEDs with associated modulated driver and power control electronics 42, single or multichannel photodetector array 43, high-speed preamplifier(s) with ambient light cancellation 44, a phase sensitive signal conditioning 45 and data acquisition circuitry 46, and a microcontrol unit (MCU) or digital signal processor (DSP) 47 and an input/output interface 48 to communicate sensor data to an operator or controller. These system elements will be discussed in the following.

Figure 5:
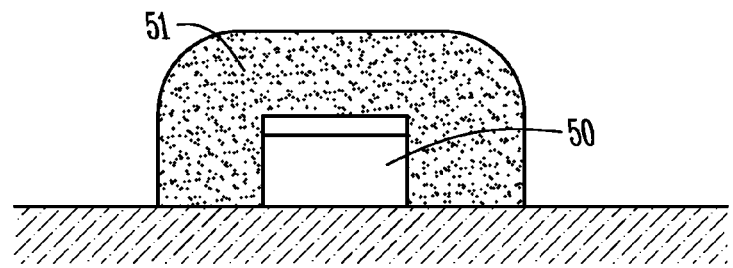
FIG. 5 show the structure of phosphor coated LED.

The light source for the invention is most preferably composed of low-color temperature phosphor coated light emitting diode(s). The structure of a phosphor LED is shown in FIG. 5. Here LED die 50 is coated with a phosphorescent compound that remits light via excitation by LED 51. The emission spectrum of phosphor coated LED's can be described as having a polychromatic emission spectrum, in that, the emission spectrum can be classified as having at least two peaks with the first one (shortest wavelength) having a first center wavelength (CWL 1) due to the emission peak of the LED and at least a second longer-wave emission center wavelength peak (CWL 2) due to the reradiation of the LED light by the phosphor coating. Depending on the phosphor composition, other peaks in the emission spectrum may be present. Phosphor coated LED's are convenient light sources for this type of invention for a number of reasons. First, white light emitting LED's are available have spectral emission characteristics that are useful for making plant biomass and pigment measurements. These LED's can be constructed to have color temperatures that span from deep violet (400 nm) to near infrared (900 nm). Second, LED's, in general, are extremely easy to use and can be modulated to megahertz frequencies. Relatively simple electronic driver circuits can be implemented and easily controlled by sensor controller electronics.

Figure 6:
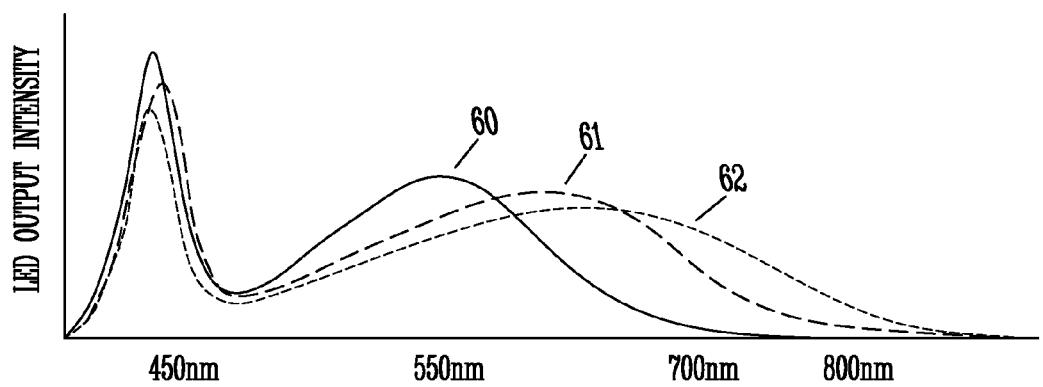
FIG. 6 show the emission spectra for 6500K (cool), 3000K (warm) and orange phosphor LED's.

Last, LED's have long lifetimes and are rugged. The typical LED will operate between 80,000 and 100,000 hours depending on the quiescent device power and operating temperature range. White light LED's using phosphor coatings over UV or blue LED emitters can have lifetimes of 40,000 to 80,000 hours. Most white light emitting LED's in production today are based on an InGaN—GaN structure, and emit blue light of wavelengths between 450 nm-470 nm blue GaN. These GaN-based, InGaN-active-layer LED's are covered by a yellowish phosphor coating usually made of cerium-doped yttrium aluminum garnet (Ce3+:YAG) crystals which have been powdered and bound in a polymer or silicone adhesive. The LED chip emits blue light, part of which is efficiently converted to a broad spectrum centered at about 580 nm (yellow) by the Ce3+:YAG. The emission color of Ce3+:YAG emitters can be modified by substituting the cerium with other rare earth elements such as terbium and gadolinium and can even be further adjusted by substituting some or all of the aluminum in the YAG with gallium. Due to the spectral characteristics of the diode, the red and green colors of objects in its blue yellow light are not as vivid as in broad-spectrum light. Manufacturing variations and varying thicknesses in the phosphor make the LED's produce light with different color temperatures, from warm yellowish to cold bluish. Spectrum of a white LED clearly showing blue light which is directly emitted by the GaN-based LED (peak at about 465 nanometers) and the more broadband stokes shifted light emitted by the Ce3+:YAG phosphor which extends from around 500 to 700 nanometers. White LEDs can also be made by coating near ultraviolet emitting LEDs with a mixture of high efficiency europium based red and blue emitting phosphors plus green emitting copper and aluminum doped zinc sulfide (ZnS:Cu, Al). This is a method analogous to the way fluorescent lamps work. The spectrum of a white LED is easily modified to create other colors by modifying the elemental components in the phosphor coating. For example, an orange, broad-band LED can be created to emit longer wavelengths of light—higher intensities of red and NIR—by using a phosphor coating containing a mixture of gadolinium, aluminum, oxygen and cerium ($Gd_3Al_5O_{12}$:Ce) over a 470 nm LED die. FIG. 6 shows the spectral graphs for cool white (6500K) 60, warm white (3000K) 61 and orange phosphor coated LED 62 emitters. Note in the graphs that the warm white and orange phosphor LED's exhibit a strong stokes shift to longer wavelengths. Good emitter output intensities in the red and NIR portions of the spectrum can be obtained for plant active plant canopy reflectance instruments or other active sensing instruments. Additionally, an NIR LED can be added to the device to further extend near infrared performance to longer wavelengths. It should be noted that there are numerous other methods, that one skilled in the art, can create different spectral outputs for LED devices (using green, yellow and red phosphor compounds) having the basic structure of the white phosphor LED.

Figure 7:
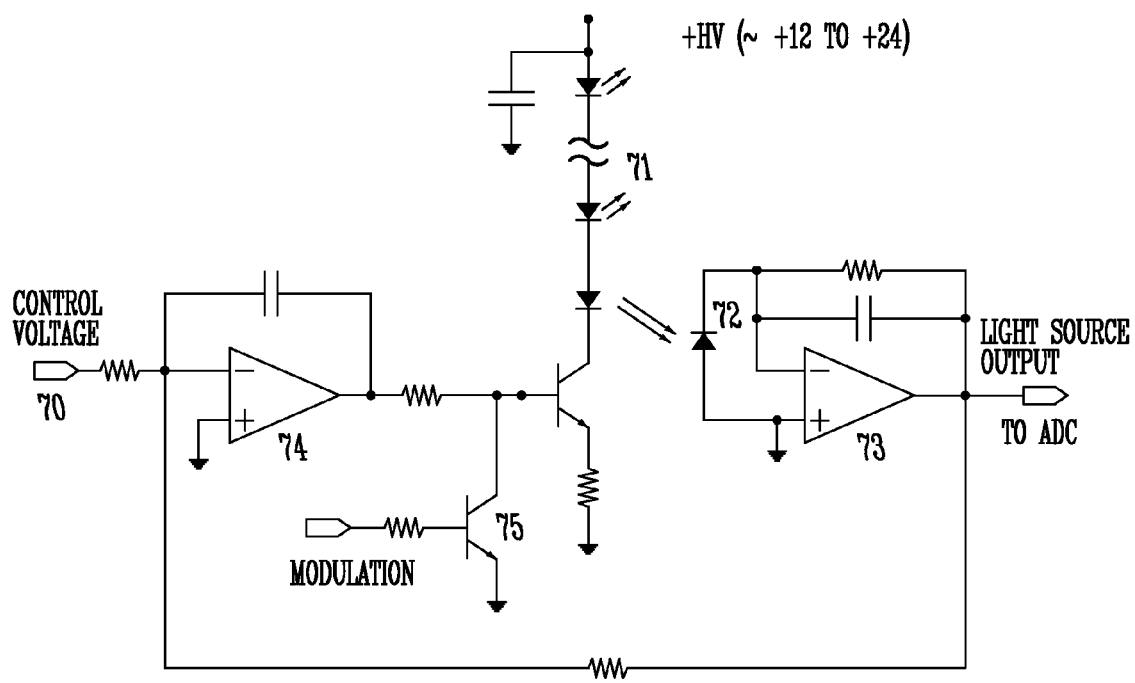
FIG. 7 shows schematically a circuit used to instrument the inventions light source.

In order to achieve good output stability with respect to thermal and aging effects, the LED sources should be adequately driven and monitored. The output intensity of LED's is very temperature dependent. Depending on the material type, an LED's output can drift between 0.4%/C and 1%/C. FIG. 7 shows schematically a circuit that provides active power control for the light source and an output intensity signal for monitoring and calibration. Control voltage 70 sets the output power of light source 71. Photodiode 72, an Infineon SFH203 (Munich, Germany), samples part of the output intensity of light source 71 and feeds this signal via amplifier 73 to servo amplifier 74. Modulation of the output signal is performed using transistor 77. Furthermore, the output of amplifier 73 can be utilized to monitor the light source intensity for purposes of calibration and diagnostics. The performance of this circuit has provided output intensity control of approximately 0.05%/C over the operating range of the invention. Many techniques have been discussed in literature detailing methods on maintaining and stabilizing light sources for photometric type measurements including the method presented here. For example, photodiode 52 can also be an array of spectrally sensitive diodes that can be utilized to monitor the same spectral bands as multi-channel photo detector array 43. In this case, each device will have a corresponding amplifier and associated detection circuitry for measuring light source spectral intensity fluctuations. Furthermore, this array of spectrally sensitive photodiodes could be designed so that spectral fluctuations in the blue, green and red portions of the emission spectrum of the light source are monitored. The resultant signals could then be utilized to correct for the overall spectral changes of the light source via mathematical curve fitting. These adjustments would account for output intensity and spectral changes of the light source. As those skilled in the art will note, there are numerous techniques and methodologies for light source power monitor/stabilization for photometric measurements discussed in engineering and scientific literature.

The detectors used in the invention are most preferably silicon photodiodes however other detector technologies such as GaAsP and the like, may be utilized as well. Silicon detectors have a typical photosensitivity spanning from 200 nm (blue enhanced) to 1200 nm. Band shaping of the detectors is performed using filtering materials such as colored filter glass, interference filters, polarizing filters or dichroic filters. Combinations of the aforementioned filter techniques can be combined in order to band-shape the radiation impinging on the photo detector surface. For example, an interference filter can be used to select a narrow bandwidth of light. In this situation, one could choose to use a 10 nm interference filters to select a band of interest within the vegetative reflectance spectrum. The use of polarizing filters may be incorporated to reduce the influence of specular reflections from the plant canopy. This is particularly useful for minimizing the effect of dew and water on a plant's reflectance characteristic as well as reducing specular reflection effects due to glossy leaf surfaces. Utilizing an array of photodetectors fitted with interference or edge filters would provide the wavelength selection needed to realize the embodiment's of this invention As one trained in the art will see, there are numerous ways in which various optical filters can be utilized to shape and control the light impinging on a photo detector or photo detector array. A unique configuration pertaining to embodiment two involves the use of linear diode array detector and diffraction grating (or linear variable filter (LVF) technology). The diffraction grating (or LVF) separates incoming, modulated light in to many wavelengths. By configuring embodiment one with a diffraction grating (or LVF)/linear array combination sensitive to the red edge region of the vegetative reflectance curve, plant chlorophyll concentrations can be measured mostly independent of soil background interference. The potential for filter configurability by an operator of the invention is possible. By specifically constructing the housing in FIG. 3 to support user insertion and removal of filters, the invention can support in-field configurability This is advantageous from the stand point that spectral selection can be easily changed when the application of the instrument is changed. Filter sets can be selected to cover all the useful vegetative indices that may be encountered for a particular agricultural landscape. For example, a filter set of red, green and NIR spectral filters can be utilized for nitrogen management (green, NIR filters) or soil mapping/weed mapping/herbicide application (red, NIR filters). The green and red band filters can be easily swapped depending on the field operation to be performed. Calibration constants for each filter combination can be stored internally in the sensor's on-board memory or recalibration can be easily performed via an integrating sphere or reflectance panel.

Referring once again to FIG. 4, both embodiments of the invention utilize a phase sensitive detector subsystem (PSD) 45 and analog-to-digital converter 46 (ADC) after each photo detector. The PSDs, sometimes referred to as lock-in amplifiers, are utilized by the invention to extract and further amplify the very small signals detected and amplified by the photodetector preamplifier(s). PSDs are often used in applications where the signal to be measured is very small in amplitude and buried in noise. Detection is carried out synchronously with modulation of the light sources. Phase sensitive detection is one of many types of band narrowing techniques that can be utilized to measure small signals. As will be apparent to those skilled in the art, other methods include the use of averaging techniques, discriminators and direct digital conversion/processing. With respect to direct digital conversion/processing, the phase sensitive acquisition component can be performed internally to a MCU or DSP by directly sampling the output of the photodiode amplifiers and performing the band pass and PSD functions digitally. By performing these operations in the digital domain, the temperature drift of the phase detector, common to analog techniques, can be eliminated. The invention performs the synchronous modulation/demodulation at a carrier frequency of 250 kHz. It should be noted that the operation of the invention is not limited to this particular modulation rate and can operate at other modulation frequencies as well with as much effectiveness. Additionally, this rate can be increased or decreased as dictated by the application. The MCU or DSP samples the output of a PSD 45 utilizing ADC 46. The resolution of the ADC is most preferably 12 bits. Each channel can sampled using a dedicated ADC or one ADC can be utilized to sample all channels via a multiplexer.

Once the detected optical signals are amplified, demodulated and quantified, the MCU or DSP 47 can calculate chlorophyll content and/or a vegetative relationship based on the reflectance values sensed.

When the sensor is fitted with a low-color temperature white LED source or long wave colored phosphor LED light source (utilizing green, yellow, orange or red phosphors or combinations thereof), calculations for plant chlorophyll status based multiple red-edge reflectance spectra can be performed a number ways. For the situation where the instrumentation has been designed to measure four or more reflectance values along the red edge, polynomial fitting may be used to fit the curve represented by the reflectance points. Subsequently, the resulting polynomial may be differentiated to find the red-edge inflection point value. The resulting wavelength will be proportional to relative shifts in the chlorophyll status of the plant. When four reflectance values are measured, the four reflectances having the center wavelengths of 670 nm, 700 nm, 740 nm and 780 nm, a preferred method is the four-point interpolation method. This method has the following mathematical for $$\rho_i = \frac{\rho_1 + \rho_4}{2}$$

$$\lambda_i = \lambda_2 + (\lambda_3 - \lambda_2) \cdot \frac{\rho_i - \rho_2}{\rho_3 - \rho_2}$$

Where $\lambda_1, \lambda_2, \lambda_3$ and $\lambda_4$ are wavelengths 670 nm, 700 nm, 740 nm and 780 nm, respectively, and $\rho_1, \rho_2, \rho_3$ and $\rho_4$ are reflectances at the corresponding wavelengths, respectively. Additionally, another red edge parameter, the red well position RWP, may be calculated using these same wavebands. The RWP interpolation has the following mathematical form $$\lambda_0 = \lambda_1 + (\lambda_2 - \lambda_1) \cdot \frac{\rho_i - \rho_2}{\rho_3 - \rho_2}$$

The RWP represent the wavelength position of a plants minimum reflectance in the red, or rather the position of maximum chlorophyll absorption. The RWP functions in a similar fashion as the REIP for predicting relative changes in plan chlorophyll status.

Other mathematical techniques for determining the REIP and RWP include Lagrangian interpolation, inverted-Gaussian modeling, regression modeling, etc. As will be apparent to one skilled in the art, the list of the aforementioned methods is not exhaustive and other common approaches to determining the REIP and RWP wavelength positions may be formulated or found in literature.

In another useful red-edge sensor embodiment, three reflectance bands, with one band reflectance band the in the red edge portion of a plant's vegetation reflectance spectra (680 nm to 760 nm), are utilized in a sensor that can distinguish between both plant nutrient and water stresses via the Canopy Chlorophyll Content Index (CCCI). The sensor utilizes two particular vegetation indexes. They are a Normalized Difference Red-Edge (NDRE) index which has the following mathematical form:

$$NDRE = \frac{\rho_3 - \rho_2}{\rho_3 + \rho_2}$$

and a standard Normalized Difference Vegetation Index (NDVI) which has the form:

$$NDVI = \frac{\rho_3 - \rho_1}{\rho_3 + \rho_1}$$

Where $\rho_1$, $\rho_2$ and $\rho_3$ are reflectances at wavelengths 670 nm, 720 nm and 800 nm (an alternate combination can include wavebands 550 nm, 720 nm and 800 nm; it should be note that there numerous waveband combinations). The NDVI as an estimate of percent plant cover and the NDRE as an indicator of plant chlorophyll content. The CCCI formula utilizes both the NDVI and NDRE indexes to calculate the impact of water and nutrient on a crop or plant.

Another embodiment of the disclosed invention utilizes a high-color temperature white LED source and detects reflectances in two visible wavebands. Nitrogen relationships in crop can be measured utilizing the two wavelength V ARI vegetation index. This particular index utilizes reflectance information measured at two visible band wavelengths and has the functional form:

$$VARI = \frac{\rho_2 - \rho_1}{\rho_2 + \rho_1}$$

In the above relationship, $\rho_1$ and $\rho_2$ are the reflectances measured at 670 nm and 550 nm respectively. In this embodiment the need for near infrared spectral emission is not required and the subsequent sensing device will perform well for detecting nitrogen stresses differentially in field crops.

Another embodiment of the disclosed invention utilizes a high-color temperature white LED source and detects reflectances in three visible wavebands. Nitrogen relationships in crop can be measured utilizing the three wavelength VARI vegetation index. This particular indicee utilizes reflectance information measured at two visible band wavelengths and has the functional form:

$$VARI = \frac{\rho_2 - \rho_1}{\rho_2 + \rho_1 - \rho_3}$$

In the above relationship, $\rho_1$, $\rho_2$ and $\rho_3$ are the reflectances measured at 670 nm and 550 nm and 470 nm respectively. As it was in the previous embodiment, the need for near infrared spectral emission is not required and the subsequent sensing device will perform well for detecting nitrogen stresses differentially in field crops or for providing phonological information pertaining to a plant.

Yet other embodiments of the disclosed invention might utilize simple ratio indexes for determining nitrogen relationships in the crop Multiple ratios can be determined simultaneously utilizing three spectral wavebands. This is demonstrated below as:

$$SRI1 = \frac{\rho_2}{\rho_1} \text{ and } SRI2 = \frac{\rho_2}{\rho_3}$$

In the above relationship, $\rho_1$, $\rho_2$ and $\rho_3$ are the reflectances measured at 670 nm and 780 nm and 730 nm respectively. Here, the vegetation indexes give exceptional sensitivity over a wide range of leaf area indexes (LAI) or biomasses. For small, early growth stage plants SRI 1 would be utilized in the invention to give added sensitivity to the VRA system while at later growth stages (high LAIs) SRI 2 would be utilized for added sensitivity to high biomass crops. Other indexes (for example VARI, NDVI, chlorophyll index (CI=SRI-1), etc. . . . ) can be utilized as well with one index sensitive to low biomass crops and the other to high biomass crops. The invention can process these indexes simultaneously with the VRA system enabled to use one or the other or both if needed for a particular field operation.

Still two other embodiments of the disclosed invention utilizes a low-color temperature white LED source or long wave colored phosphor LED source (utilizing green, yellow, orange or red phosphors or combinations thereof) and detects reflectances in two and three wavebands. Crop status can also be measured utilizing the two or three wavelength red-edge VARI vegetation index. The particular indices utilize reflectance information measured at one or two visible wavelengths and one red edge wavelength. The indices have the functional forms:

$$VARI(\text{Red\_Edge\_2\_Band}) = \frac{\rho_2 - \rho_1}{\rho_2 + \rho_1}$$

$$VARI(\text{Red\_Edge\_3\_Band}) = \frac{\rho_2 - 1.7 \times \rho_1 + 0.7 \times \rho_3}{\rho_2 + 2.3 \times \rho_1 - 1.3 \times \rho_3}$$

In the above relationship, $\rho_1$, $\rho_2$ and $\rho_3$ are the reflectances measured at 670 nm, 710 nm and 470 nm respectively. As will be apparent to one skilled in the art, there numerous other combinations of wavebands and indices that the principles of this inventive instrument can incorporate.

Data calculated by the sensor's processing component is communicated to an operator or system controller via input/output interface 48. In the case of a handheld instrument, the I/O interface may take the form of a keypad and display. If the invention is incorporated into a sprayer or mapping system having several sensors networked together, the I/O interface will most preferably be a networkable serial port such a as RS485 port or CAN 2.0b port.

Applications of Use—Methods

Figure 8:
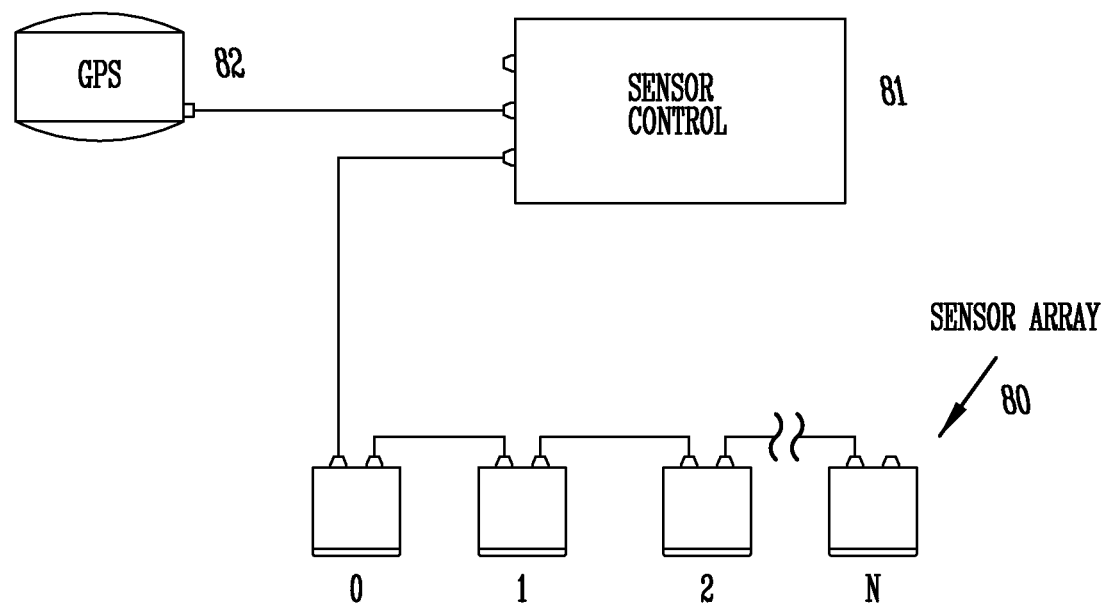
FIG. 8 shows diagrammatically a sensor based mapping system.

FIG. 8 show a block diagram of the invention incorporated into a system that is used to map plant status. Elements of the system include sensor array 80, sensor controller 81, and GPS 82. The sensor array 80 may also be referenced throughout as an example of an optical sensing system and the sensor controller 81 may be referenced simply as a controller 81. The controller 81 may be operatively connected to an applicator.

The role of the sensor in this system is to measure the chlorophyll status and/or biomass properties of the plant being mapped. Data produced by the sensor are collected by the system controller for storage and later analysis. Each sensor point is geo-referenced using the GPS connected the system controller. There are two primary ways in which mapping can be performed the system. First, the map collected by the system can be all-inclusive, that is, every data point measured by the sensor can be stored away in the controller's memory for later retrieval and analysis. Second, the sensor/controller can be programmed with a defined set of rules so as to distinguish poor performing regions of a landscape from good or healthy regions and vice versa and store only the poor performing regions. This mode of operation saves storage space in the controller and reduces the amount of data processing that has to be performed. As an example, the mapping systems could be mounted to the mower machinery for a golf course. When the course personnel perform their weekly mowing operations, the mapping systems would scout for problem areas of the turf. For turf management operations, this mode would be most useful because regions of turf that are suffering from stress (disease, water, nutrient, and so forth) or are beginning to suffer. The mapping systems would flag affected areas for the turf manager to scout out visually.

Figure 9:
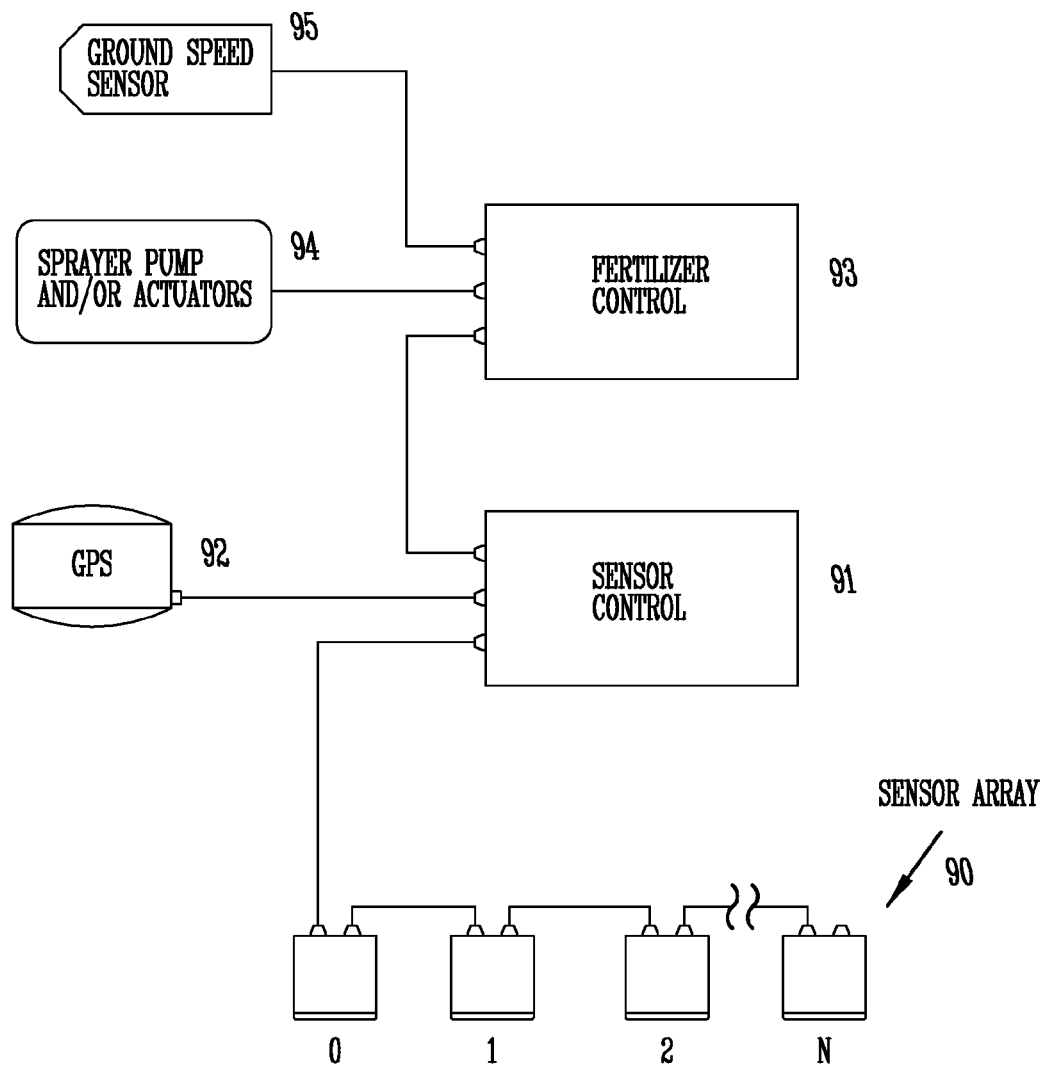
FIG. 9 shows diagrammatically a sensor based variable-rate applicator system.

FIG. 9 show a block diagram of the invention incorporated into a system that is used for applying an agricultural product. Elements of the system include sensor array 90 (or optical sensing system), sensor controller 91, GPS 92, fertilizer controller 93, sprayer pumps/actuators 94 and ground speed sensor 95. The functions of the sensor controller 91 and the fertilizer controller 93 may be combined as a single controller. The sprayer pumps/actuators 94 may form at least a part of an applicator. For applying an agricultural product.

The agricultural product may be either in liquid or solid form and may be, but not limited to, a nutrient, mineral, herbicide or fungicide or a combination of the aforementioned materials. The variable rate control system can be mounted to a commercial sprayer or tractor mounted sprayer system. GPS can be incorporated in the system when a map is required of plant canopy characteristics for later analysis. In addition, to mapping plant characteristics, material dispensation rates can be mapped as well. GPS is also required when applying fertilizer referenced to an N sufficient reference strip. In this situation, a region of the field is given an N-rate that totally meets the needs of the crop to grow without loss of yield and apply a lower amount of pre-emergent fertilizer (only the amount to initially cause the crop to grow) to the remainder of the field. At a time later in the growing season, the producer will apply a second treatment to the remainder of the field using the sensor readings for the N sufficient region of the field. Readings from the N insufficient parts of the field will be compared with readings from the N sufficient regions of the field. The controller will use the sensor measurements to calculate the appropriate rate of fertilizer to apply to the N insufficient portion of the field in order to prevent yield loss. As mentioned earlier, the growth stage of the plant will have an impact on the usefulness of a particular vegetation index based on the selection of the spectral components utilized to perform the index calculation. For example, and NDVI or other vegetation index based on red and near infrared light will be most effective at quantifying plant biomass at low leaf area indexes (LAI), that is, small plants where as an NDRE (same mathematical form as and NDVI) based on red-edge and near infrared spectral components will have be most effective at quantifying plant biomass at high LAIs. As such the system disclosed can automatically (or set manually) to switch between vegetation indexes that are either sensitive to low LAI or high LAI plants in order to optimize system sensitivity to plant biomass and to optimally apply agrochemicals. This is important because many vegetation indexes tend to have poor or limited sensitivity to crops at either low biomasses or high biomasses (stated otherwise as low LAI or high LAI).

Figure 10:
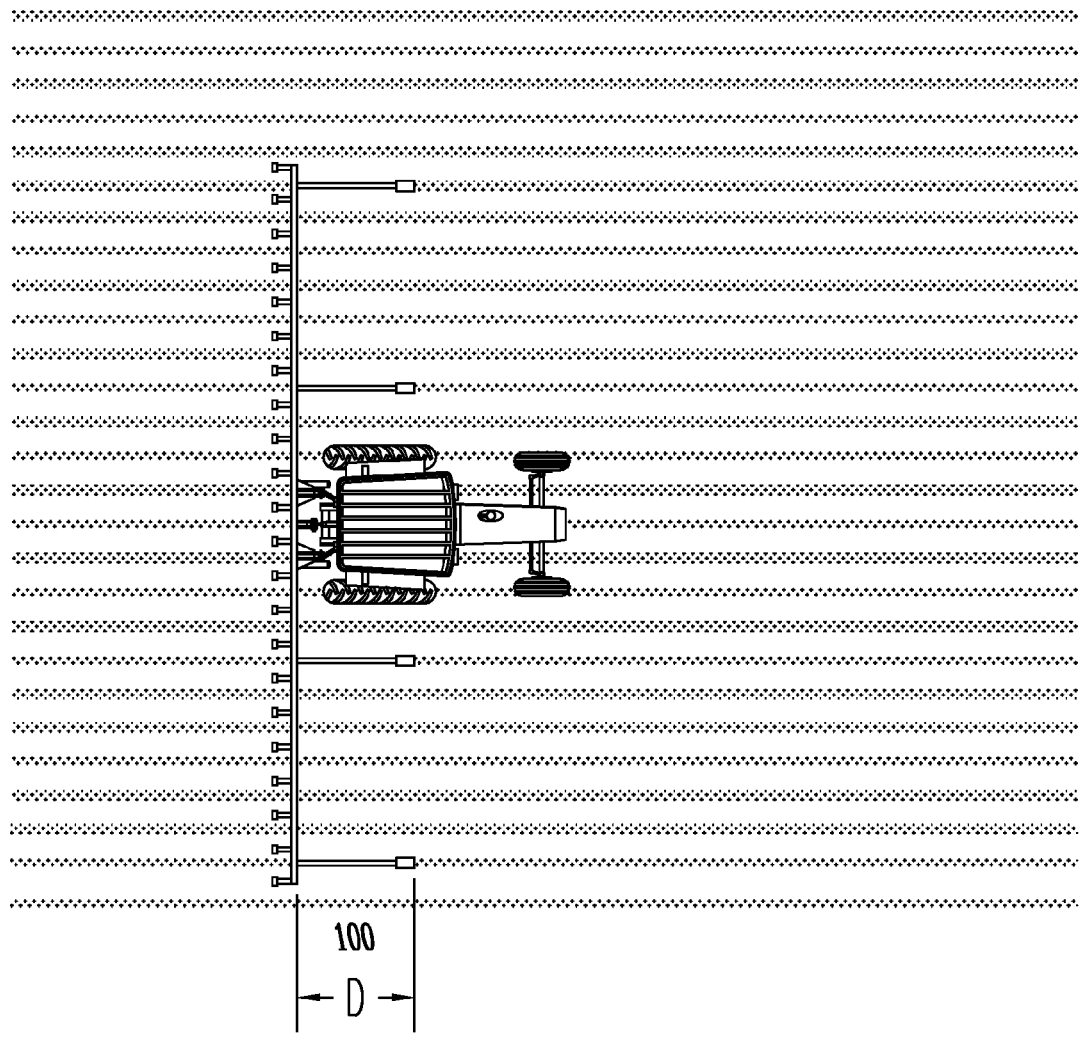
FIG. 10 illustrates the necessary sensor-to-spray nozzle separation for compensating for plant canopy periodicity and random leaf orientation.

FIG. 10 shows an applicator example with the sensor stood-off from the spray nozzles. When designing variable rate application system, the obvious approach is to physically locate the sensor close or next to the sprayer nozzle. However, because of the random orientation of most plant canopies the sensor should be separated from the sprayer nozzles by a distance D 100. This allows the sensing instrument to collect data on a portion of the crop, so as to average the spatial variability, before applying an agricultural product. The separation distance D between the sensor and sprayer nozzles should most preferably be greater than 3 feet. In operation, the variable rate system will collect data for D feet and apply an agricultural product over D feet while sensing the next D separation distance. Another strength of a red-edge measurement sensor, as disclosed above, is that the measurement made by the instrument is relatively invariant with respect to varying plant population. This is critical for making N fertilizer recommendations on fields that have had crops planted utilizing variable rate seeding techniques. With a biomass sensor, a seed rate map would have to be utilized in conjunction with the variable rate application algorithm in order to compensate for changes in plant biomass resulting from the seeding operation.

The benefits of a system such as the one just described are both economic and environmental. By using less fertilizer and only applying it where the crop needs it, the producer can lower his use of fertilizer and thus lower his production cost. Additionally, by using less fertilizer and only applying it where the crop needs it, reduced run-off and leaching into our watershed occurs. Because the present invention produces its own source of light, the measurements that it makes is not influenced by ambient light conditions. Applicator equipment fitted with sensors of this type can be operated around the clock at night and under full sun.

According to another aspect of the present invention a Water Invariant Chlorophyll Index (WICI) is provided to assist in minimizing the effect of water stress when making a chlorophyll type measurement. It has been tested on dryland corn and wheat although may be used for other types of crops as well.

Below are two examples of WICI's. The basic form of a WICI index is comprised of the ratio of two DVI's (Difference Vegetation Index) using a minimum of three spectral bands shown below $$WICI1 = \frac{DVI|_{\lambda_2}^{\lambda_3}}{DVI|_{\lambda_1}^{\lambda_3}} = \frac{\rho_3 - \rho_2}{\rho_3 - \alpha \cdot \rho_1}$$

$$WICI2 = \frac{DVI|_{\lambda_2}^{\lambda_3}}{DVI|_{\lambda_1}^{\lambda_2}} = \frac{\rho_3 - \rho_2}{\rho_2 - \alpha \cdot \rho_1}$$

where $\rho_1$, $\rho_2$ and $\rho_3$ represent the reflectances at 670 nm, 730 nm and 800 nm, $\alpha$ is a scalar ($0 \leq \alpha \leq 2$).

It is theorized that better delta matching can be obtained while still preserving the information content of the red band via the use of scalar $\alpha$. On test data this appeared to be the case.

WICI 1 was designed specifically for use in cereals while WICI 2 was designed for use in corn.

The concept involves the assumption that a plant under short term water stress will have reflectance offsets that are nearly identical for wavebands closely located together. Consider WICI 1 shown in the below equation with water stress offsets added.

$$WICI1 = \frac{(\rho_3 + \delta_{w3}) - (\rho_2 + \delta_{w2})}{(\rho_3 + \delta_{w2}) - (\rho_1 + \delta_{w1})}$$

where $\delta_{w1}$, $\delta_{w2}$, and $\delta_{w3}$ are the water stress reflectances for each spectral band.

If we assume that $$\delta_{w1} \approx \delta_{w2} \approx \delta w_{w3} \approx \delta_w$$

and substitute the right hand of the above equation into the previous equation and rearrange terms, we obtain the following equation.

$$\begin{aligned} WICI1 &= \frac{(\rho_3 + \delta_{w3}) - (\rho_2 + \delta_{w2})}{(\rho_3 + \delta_{w2}) - (\rho_1 + \delta_{w1})} \\ &= \frac{(\rho_3 + \delta_w) - (\rho_2 + \delta_w)}{(\rho_3 + \delta_w) - (\rho_1 + \delta_w)} \\ &= \frac{(\rho_3 - \rho_2) + (\delta_w - \delta_w)}{(\rho_3 - \rho_1) + (\delta_w - \delta_w)} \\ &= \frac{(\rho_3 - \rho_2)}{(\rho_3 - \rho_1)} \end{aligned}$$

Note also, that in certain circumstances, the delta terms may be other mutual offset phenomena, for example, soil back ground. In addition to the representative examples of computations for calculating WICI, the present invention contemplates other variations. For example, more than three spectral bands may be used in the calculations, or multiple WICI's may be separately computed and combined.

The resulting WICI, once calculated, may be used to assist in determining the proper treatment for a plant. The treatment may involve applying agrochemicals using an applicator. The process of making the measurements, the calculations, and the treatment may be part of a real-time process is performed onboard an agricultural implement within the field. In such a process, a system may be used which includes an optical system which includes one or more optical sensors, an applicator for applying treatment, and a controller operatively connected to the optical system and the applicator which performs calculations and controls the applicator.

Although various embodiments have been described, the present invention contemplates numerous variations. For example, although a water invariant chlorophyll index is described, the present invention contemplates that other types of water indexes may be used, including that described in Zygielbaum et al. (2009), "Non-destructive detection of water stress and estimation of relative water content in maize", Geophysical Research Letters, Vol. 36, L12403, herein incorporated by reference in its entirety. In addition, other types of indexes may be used to assist in determining the proper treatment for plants. This may include a Chlorophyll Content Index (CCCI), such as that described in Barnes et al. (2000), Coincident detection of crop water stress, nitrogen status, and canopy density using ground—based multispectral data, *Proc. 5th Intern. Conf. on Precision Agriculture and Other Resource Management,* 38 TRANSACTIONS OF THE ASAE, herein incorporated by reference in its entirety.

Although various embodiments of this invention have been described in detail above, those skilled in the art will readily appreciate that many modifications are possible in the embodiments given without materially departing from the novel teachings and advantages of this invention. Accordingly, various modifications, adaptations, and combinations or various features of the described embodiments can be practiced without departing from the scope of the invention as set forth in the claims.

What is claimed is:

1. A method of treating plants, comprising:
   measuring optical properties of a plant using at last three spectral bands;
   calculating in a computational device at least two difference vegetative indexes using the optical properties, each of the at least two vegetative indexes correlating to one or more plant growth parameters;
   calculating in the computational device a water invariant chlorophyll index from the at least two difference vegetative indexes using the at least three spectral bands; and
   treating one or more of the plants based on the water invariant chlorophyll index;
   wherein the water invariant chlorophyll index comprises a ratio of two of the difference vegetative indexes each using the at least three spectral bands and wherein the difference vegetative indexes and the at least three spectral bands are selected to minimize effect of water stress when making a chlorophyll type measurement.

2. The method of claim 1 wherein the method is performed in real-time.

3. The method of claim 1 wherein the measuring optical properties of a plant using a plurality of spectral bands comprises:
   (a) simultaneously projecting light of a first, visible wavelength from a solid-state polychromatic light source, and light of a second, infrared wavelength from the light source, modulating the light source, and setting and monitoring optical power of the light source;
   (b) receiving reflected visible light originating from the light source in a reflected light receiver comprising a first photodetector sensitive to visible light, and reducing the effects of ambient light on the first photodetector in an ambient light compensation means to provide a first output;
   (c) configuring the photodetectors for each of the plurality of spectral bands by applying at least one spectral selectivity means to at least one of the photodetectors, wherein the spectral selectivity means is fitted to removably attach to the photodetector;
   (d) positioning a second photodetector sensitive to infrared light to receive reflected infrared light originating from the light source, and reducing the effects of ambient light on said second photodetector in an ambient light compensation means to provide a second output;
   (e) distinguishing the light originating from said light source and reflected by the object from ambient light.

4. The method of claim 1 wherein the measuring optical properties of a plant using a plurality of spectral bands comprises:
   (a) simultaneously projecting light of a first, visible wavelength from a first solid-state polychromatic light source, light of a second, red-edge wavelength from a second solid-state polychromatic light source, and light of a third, infrared wavelength from a third light source, modulating the first, second and third light sources, and setting and monitoring optical power of the first and second and third light sources;
   (b) receiving reflected visible light originating from the first light source in a reflected light receiver comprising a first photodetector sensitive to visible light, and reducing the effects of ambient light on the first photodetector in an ambient light compensation means to provide a first output;
(c) configuring photodetectors for each of the plurality of spectral bands by applying at least one spectral selectivity means to at least one of the photodetectors, wherein the spectral selectivity means is fitted to removably attach to the photodetector;
(d) positioning a second photodetector sensitive to infrared light to receive reflected infrared light originating from the light source, and reducing the effects of ambient light on said second photodetector in an ambient light compensation means to provide a second output;
(e) distinguishing the light originating from said light sources and reflected by the object from ambient light.

5. The method of claim 1, wherein the step of treating comprises applying an agricultural treatment to the one or more plants with an applicator.

6. The method of claim 1 wherein the method is performed on an agricultural implement within a field.

7. A method of treating plants, comprising:
measuring optical properties of one or more plants across three or more spectral bands;
calculating in a computational device at least two difference vegetative indexes using the optical properties, each of the at least two difference vegetative indexes correlating to one or more plant growth parameters;
calculating in the computational device a water invariant chlorophyll index from the at least two difference vegetative indexes using the three or more spectral bands; and
treating the plants based on the water invariant chlorophyll index;
wherein the water invariant chlorophyll index comprises a ratio of two of the difference vegetative indexes each using the three or more spectral bands and wherein the difference vegetative indexes and the three or mere spectral bands are selected to minimize effect of water stress when making a chlorophyll type measurement.

8. The method of claim 7 wherein the step of treating is performed using an applicator.

9. The method of claim 7 wherein the method is performed on an agricultural implement within a field.

10. A system for treating plants, comprising:
an optical sensing system configured to measure optical properties of one or more plants across three or more spectral bands;
an applicator for selectively applying treatment to the plants;
a controller operatively connected to the optical sensing system and the applicator and configured to (a) calculate at least two difference vegetative indexes using the optical properties, each of the at least two difference vegetative indexes correlating to one or more plant growth parameters, (b) calculate a water invariant chlorophyll index from at least two difference vegetative indexes using the three or more spectral bands, and (c) control the applicator to provide for selectively applying treatment to the plants based on the water invariant chlorophyll index;
wherein the optical sensing system comprises a light sensor for measuring the reflectance of an object, comprising: (a) a polychromatic light source simultaneously emitting visible light and infrared light with a modulator of the light source, and apparatus to set and monitor optical power of the light source; and (b) a reflected light receiver comprised of an array of photodetectors comprised of at least one photodetector sensitive to visible light positioned to receive reflected light originating from the light source and including ambient light compensation means for reducing the effects of ambient light on the photodetector and a first output, and at least one photodetector sensitive to nonvisible light positioned to receive reflected light originating from said light source and including an ambient light compensator for reducing the effects of ambient light on said second photodetector and a second output;
wherein the water invariant chlorophyll index comprises a ratio of two of the difference vegetative indexes each using the three or more spectral bands and wherein the difference vegetative indexes and the three or more spectral bands are selected to minimize effect of water stress when making a chlorophyll type measurement.

11. A system for treating plants, comprising:
an optical sensing system configured to measure optical properties of one or more plants across a three or more spectral bands;
an applicator for selectively applying treatment to the plants;
a controller operatively connected to the optical sensing system and the applicator and configured to control the application of the treatment based on properties of the one or more plants determined from the optical properties, and a plurality of indexes that relate the properties of the one or more plants to the optical properties;
wherein the plurality of indexes include at least one index selected based on leaf area;
wherein the plurality of indexes include at least one water invariant chlorophyll index;
wherein the water invariant chlorophyll index comprises a ratio of two difference vegetative indexes each using three or more spectral bands and wherein the difference vegetative indexes and the three or more spectral bands are selected to minimize effect of water stress when making a chlorophyll type measurement.

12. The system of claim 11 wherein a first of the plurality of indexes is associated with a first of the spectral bands and a second of the plurality of indexes is associated with a second of the spectral hands.

13. The system of claim 11 wherein the plurality of bands include lbur or more bands.

14. A method of treating plants, comprising:
measuring optical properties of a plant using a plurality of spectral bands;
calculating in a computational device at least two vegetative indexes using the optical properties, each of the at least two vegetative indexes correlating to one or more plant growth parameters, wherein a first of the vegetative indexes is used for low leaf area index and a second of the vegetative indexes is used for a high leaf area index and wherein at least one of the vegetative indexes is a water invariant chlorophyll index;
wherein the water invariant chlorophyll index comprises a ratio of two difference vegetative indexes each using a minimum of three spectral bands and selected to minimize effect of water stress when making a chlorophyll type measurement.

15. The method of claim 14 wherein the plurality of spectral bands include three or more bands.

16. The method of claim 14 wherein the plurality of spectral bands include four or more bands.

17. The method of claim 14 wherein at least one of the plurality of spectral bands is associated with chlorophyll.

18. The method of claim 14 wherein one of the plurality of spectral bands is associated with water.

* * * * *